United States Patent
Nager

(10) Patent No.: US 10,064,940 B2
(45) Date of Patent: Sep. 4, 2018

(54) MULTIFUNCTIONAL RADIATION DELIVERY APPARATUS AND METHOD

(71) Applicant: Siva Therapeutics Inc., Boulder, CO (US)

(72) Inventor: Zachary Nager, Boulder, CO (US)

(73) Assignee: Siva Therapeutics Inc., Boulder, CO (US)

( * ) Notice: Subject to any disclaimer, the term of this patent is extended or adjusted under 35 U.S.C. 154(b) by 218 days.

(21) Appl. No.: 14/567,077

(22) Filed: Dec. 11, 2014

(65) Prior Publication Data
US 2015/0162109 A1    Jun. 11, 2015

Related U.S. Application Data

(60) Provisional application No. 61/914,786, filed on Dec. 11, 2013.

(51) Int. Cl.
*A61N 5/06* (2006.01)
*A61K 41/00* (2006.01)

(52) U.S. Cl.
CPC ............ *A61K 41/0052* (2013.01); *A61N 5/06* (2013.01); *A61N 2005/0633* (2013.01); *A61N 2005/0642* (2013.01); *A61N 2005/0652* (2013.01); *A61N 2005/0659* (2013.01)

(58) Field of Classification Search
CPC .............. A61N 5/06; A61N 2005/0633; A61N 2005/0642; A61N 2005/0631
See application file for complete search history.

(56) References Cited

U.S. PATENT DOCUMENTS

| | | | |
|---|---|---|---|
| 1,645,307 | A | 10/1927 | Snow |
| 2,149,743 | A | 3/1939 | Newick |
| 4,822,335 | A | 4/1989 | Kawai et al. |
| 5,042,494 | A | 8/1991 | Alfano |
| 5,149,319 | A | 9/1992 | Unger |

(Continued)

FOREIGN PATENT DOCUMENTS

| | | |
|---|---|---|
| EP | 1645307 | 4/2006 |
| EP | 2149743 | 2/2010 |

(Continued)

OTHER PUBLICATIONS

"Patent Royalties Extending Beyond Expiration: An Illogical Ban From Brulotte to Scheiber," 7 pages.

(Continued)

*Primary Examiner* — Joseph Stoklosa
*Assistant Examiner* — Sean W Collins
(74) *Attorney, Agent, or Firm* — Sheridan Ross P.C.

(57) ABSTRACT

Embodiments of this invention relate to a flexible, multifunctional apparatus for delivering electromagnetic energy to a target surface. The apparatus may be used in a variety of applications and environments, including but not limited to, medical therapies and treatments. The apparatus comprises at least one primary radiation source, in some embodiments an array of light-emitting diodes, and is capable of emitting electromagnetic radiation in the range from 800 to 950 nanometers. The apparatus comprises a moveable arm for positioning the radiation source relative to the target surface. The apparatus is useful for photothermal therapy in the treatment of medical conditions, including cancer.

1 Claim, 2 Drawing Sheets

(56) References Cited

U.S. PATENT DOCUMENTS

| | | | |
|---|---|---|---|
| 5,300,097 A | 4/1994 | Lerner et al. | |
| 5,358,503 A | 10/1994 | Bertwell et al. | |
| 5,560,933 A | 10/1996 | Soon-Shiong et al. | |
| 5,569,448 A | 10/1996 | Wong et al. | |
| 5,639,725 A | 6/1997 | O'Reilly et al. | |
| 5,728,090 A | 3/1998 | Martin et al. | |
| 5,944,748 A | 8/1999 | Mager et al. | |
| 6,165,440 A | 12/2000 | Esenaliev | |
| 6,201,425 B1 | 3/2001 | Kartschoke et al. | |
| 6,210,425 B1 | 4/2001 | Chen | |
| 6,274,552 B1 | 8/2001 | Tamarkin et al. | |
| 6,344,272 B1 | 2/2002 | Oldenburg et al. | |
| 6,354,297 B1 | 3/2002 | Eiseman | |
| 6,375,634 B1 | 4/2002 | Carroll | |
| 6,428,811 B1 | 8/2002 | West et al. | |
| 6,528,485 B1 | 3/2003 | Veronese et al. | |
| 6,530,944 B2 | 3/2003 | West et al. | |
| 6,645,230 B2 | 11/2003 | Whitehurst | |
| 6,645,517 B2 | 11/2003 | West et al. | |
| 6,866,678 B2 | 3/2005 | Shenderova et al. | |
| 6,955,684 B2 | 10/2005 | Savage, Jr. et al. | |
| 7,118,563 B2 | 10/2006 | Weckwerth et al. | |
| 7,125,416 B2 | 10/2006 | Kent et al. | |
| 7,156,865 B2 | 1/2007 | Waldmann | |
| 7,189,983 B2 | 3/2007 | Aguirre et al. | |
| 7,220,254 B2 | 5/2007 | Altshuler et al. | |
| 7,229,841 B2 | 6/2007 | Tamarkin et al. | |
| 7,264,629 B2 | 9/2007 | Simkin et al. | |
| 7,276,058 B2 | 10/2007 | Altshuler et al. | |
| 7,387,900 B2 | 6/2008 | Tamarkin et al. | |
| 7,422,598 B2 | 9/2008 | Altshuler et al. | |
| 7,488,102 B2 | 2/2009 | Brukilacchio | |
| 7,517,101 B2 | 4/2009 | Tobin | |
| 7,763,035 B2 | 7/2010 | Melkent et al. | |
| 7,790,066 B2 | 9/2010 | Wang et al. | |
| 7,815,668 B2 | 10/2010 | Butler | |
| 7,835,778 B2 | 11/2010 | Foley et al. | |
| 7,840,253 B2 | 11/2010 | Tremblay et al. | |
| 7,887,533 B2 | 2/2011 | Barolet et al. | |
| 8,134,132 B2 | 3/2012 | Middlemass et al. | |
| 8,278,841 B2 | 10/2012 | Brukilacchio | |
| 8,328,796 B2 | 12/2012 | Altshuler et al. | |
| 8,480,720 B2 | 7/2013 | Weisbart et al. | |
| 8,481,982 B2 | 7/2013 | Johnson et al. | |
| 8,486,056 B2 | 7/2013 | Irwin | |
| 8,557,568 B2 | 10/2013 | Cheong et al. | |
| 8,611,563 B2 | 12/2013 | Davidson | |
| 8,722,375 B2 | 5/2014 | Costas et al. | |
| 2002/0128695 A1 | 9/2002 | Harth et al. | |
| 2004/0093043 A1 | 5/2004 | Edel et al. | |
| 2004/0122492 A1* | 6/2004 | Harth | A61N 5/0613 607/88 |
| 2004/0186536 A1 | 9/2004 | Osendowski | |
| 2005/0055015 A1 | 3/2005 | Buzawa | |
| 2006/0206173 A1* | 9/2006 | Gertner | A61N 5/0616 607/88 |
| 2006/0259102 A1 | 11/2006 | Slatkine | |
| 2006/0287696 A1 | 12/2006 | Wright et al. | |
| 2007/0032843 A1 | 2/2007 | Hsu | |
| 2007/0073365 A1* | 3/2007 | Butler | A61N 5/0613 607/88 |
| 2007/0225778 A1 | 9/2007 | Heacock et al. | |
| 2008/0096156 A1* | 4/2008 | Rose | A61C 1/0015 433/29 |
| 2008/0108982 A1* | 5/2008 | Barolet | A61B 18/203 606/9 |
| 2008/0125772 A1 | 5/2008 | Stone et al. | |
| 2008/0160090 A1 | 7/2008 | Oraevsky et al. | |
| 2009/0088824 A1 | 4/2009 | Baird et al. | |
| 2009/0306646 A1* | 12/2009 | Turner | A61B 18/18 606/33 |
| 2010/0174222 A1 | 7/2010 | McDaniel | |
| 2010/0286674 A1 | 11/2010 | Ben-Yakar et al. | |
| 2012/0041523 A1 | 2/2012 | Solomon et al. | |
| 2012/0123507 A1 | 5/2012 | Whitehurst | |
| 2012/0150044 A1 | 6/2012 | Kim | |
| 2012/0263793 A1 | 10/2012 | Vitaliano | |
| 2015/0224295 A1* | 8/2015 | Li | A61N 1/36 604/20 |

FOREIGN PATENT DOCUMENTS

| | | |
|---|---|---|
| WO | WO 9321842 | 11/1993 |
| WO | WO 99/24077 | 5/1999 |
| WO | WO 2006/122222 | 11/2006 |
| WO | WO 2007/149221 | 12/2007 |
| WO | WO 2008/125772 | 10/2008 |
| WO | WO 2010/085651 | 7/2010 |
| WO | WO 2010/123993 | 10/2010 |
| WO | WO 2012/057819 | 5/2012 |
| WO | WO 2012/125693 | 9/2012 |
| WO | WO 2013/095736 | 6/2013 |
| WO | WO 2013/165499 | 11/2013 |

OTHER PUBLICATIONS

Hamburg, FDA's Approach to Regulation of Products of Nanotechnology, Science, 2012, vol. 336, pp. 299-300.

Huang et al., "Plasmonic photothermal therapy (PPTT) using gold nanoparticles," Lasers Med Sci, 2008, vol. 23, pp. 217-228.

Jacques et al., Laser-Tissue Interaction X: Photochemical, Photothermal, and Photomechanical, SPIE, 1999, vol. 3601, pp. 165-176.

Jain, "Transport of Molecules, Particles, and Cells in Solid Tumors," Annual Review of Biomedical Engineering, 1999, vol. 1, pp. 241-263, 30 pages.

Jordan et al., "Endocytosis of dextran and silan-coated magnetite nanoparticles and the effect of intracellular hyperthermia on human mammary carcinoma cells in vitro," Journal of Magnetism and Magnetic Materials, 1999, vol. 194(1-3), pp. 185-196.

Lin et al., "Cavitation and acoustic emission around laser-heated microparticles," Applied Physics Letters, 1998, vol. 72(22), pp. 2800-2802.

Loo et al., "Nanoshell-Enabled Photonics-Based Imaging and Therapy of Cancer," Technology in Cancer Research & Treatment, 2004, vol. 3(1), pp. 33-40.

Oldenburg et al., "Nanoengineering of optical resonances," Chemical Physics Letters, 1998, vol. 288, pp. 243-247.

O'Neal et al., "Photo-thermal tumor ablation in mice using near infrared-absorbing nanoparticles," Cancer Letters, 2004, vol. 209, pp. 171-176.

Peleg et al., "Nonlinear optical measurement of membrane potential around single molecules at selected cellular sites," Proc. Natl. Acad. Sci. USA, 1999, vol. 96, pp. 6700-6704.

Schutt et al., "Applications of Magnetic Targeting in Diagnosis and Therapy—Possibilities and Limitations: A Mini-Review," Hybridoma, 1997, vol. 16(1), 9 pages.

Weintraub, "Gold particles could deliver cancer drugs," The Boston Globe, 2012, Retrieved from https://www.bostonglobe.com/business/2012/12/24/astrazeneca-waltham-unit-aims-use-gold-nanoparticles-deliver-cancer-drugs-directly-tumors/Rq3b1KKx0hJWgkCxt5KVcO/story.html, retrieved on Aug. 31, 2015, 4 pages.

Whelan et al., "NASA Light Emitting Diode Medical Applications from Deep Space to Deep Sea," American Institute of Physics Conference Proceedings 552, 2001, 18 pages.

Official Action for U.S. Appl. No. 13/202,311, dated Sep. 20, 2012, 10 pages.

\* cited by examiner

MULTIFUNCTIONAL RADIATION DELIVERY APPARATUS AND METHOD

CROSS-REFERENCE TO RELATED APPLICATION

This application is a non-provisional application of and claims priority to U.S. Ser. No. 61/914,786 entitled "Multifunctional Radiation Delivery Apparatus and Method" filed on Dec. 11, 2013, the entire disclosure of which is incorporated herein by reference.

FIELD OF THE INVENTION

This invention relates to a flexible, multifunctional apparatus for delivering electromagnetic energy to a target surface. The apparatus may be used in a variety of applications and environments, including but not limited to, medical therapies and treatments. The apparatus comprises at least one primary radiation source, and is capable of emitting electromagnetic radiation in the range from 800 to 950 nm.

BACKGROUND OF THE INVENTION

Electromagnetic radiation is known to have many benefits. For example in the area of medical therapies, wavelengths of 680, 730 and/or 880 nanometers have been shown to increase cell growth and speed wound healing (especially when combined with hyperbaric oxygen), and have been used to activate photoactive agents for various cancer treatments. (See Whelan et al., "NASA Light Emitting Diode Medical Applications From Deep Space to Deep Sea," Space Technology and Applications International Forum—2001, American Institute of Physics, pp. 35-45 (2001).)

In the case of infrared heating, an infrared heating system optimally raises the temperature of a target with the least energy consumption. Such a system may comprise a device that can directly convert its electrical power input to a radiant electromagnetic energy output, with the chosen single or narrow band wavelengths that are aimed at a target, such that the energy comprising the irradiation is partially or fully absorbed by the target and converted to heat. The more efficiently the electrical input is converted to radiant electromagnetic output, the more efficiently the system can perform. The more efficiently the radiant electromagnetic waves are aimed to expose only the desired areas on the target, the more efficiently the system will accomplish its work. The radiation emitting device chosen for use should have an instant "on" and instant "off" characteristic such that when the target is not being irradiated, neither the input nor the output energy is wasted. The more efficiently the exposed target absorbs the radiant electromagnetic energy to directly convert it to heat, the more efficiently the system can function.

In addition, for a particular system or therapy, care must be taken to properly select the output wavelengths such that it matches the absorptive characteristic of the target. The wavelengths required will be different for different targeted applications. Unfortunately, most radiation delivery systems either provide a wide, multichromatic distribution of wavelengths to a target, or a select few wavelengths of monochromatic radiation.

In addition, current products requiring high intensity uniform illumination over the spectral range including ultraviolet (UV) to infrared (IR) are based primarily on mercury arc lamps, which are expensive, inefficient, contain toxic materials dangerous to the environment, short lived, and operated by costly and high voltage ballasts. Xenon and metal halide short arc lamps have also been used, as have tungsten halogen sources. As with mercury arc lamps, both xenon and metal halide lamps also contain toxic materials, expensive power supplies and ballasts and suffer from short lifetimes, requiring frequent replacement, interruptions in progress, and additional costs associated with both the labor for replacement and the lamp itself. A further disadvantage of tungsten halogen based systems is the relatively low output particularly for short blue and UV wavelengths. Additionally, very large voltages are required from power supply ballasts on the order of kilovolts to start the lamps. These high voltages can damage sensitive medical and industrial instrumentation due to the emitted electromagnetic pulse. In addition to these issues with the use of mercury, xenon, and metal halide lamps, recent concern over the use of highly toxic materials has fueled the search for alternatives to the arc lamps and improvements over the low output and poor lifetime of tungsten based lamps. Additionally, the warm up time for mercury, xenon and metal halide lamp systems is relatively long and they cannot be pulsed on and off effectively.

Likewise, quartz infrared heating lamps, which are well known in the art and are used for various process heating operations, will often produce a peak output in the 0.8 to 1 micrometer range. Although the output may peak between 0.8 and 1 micrometers, these lamps have substantial output in a wide continuous set of wavelength bands from the ultraviolet (UV) through the visible and out to about 3.5 micrometers in the middle-infrared. Quartz lamps are "slow on" and "slow off" devices and cannot practically be rapidly pulsed at high frequencies.

In addition, many optical energy applications require high intensity, spatially uniform, light that does not significantly heat the surrounding environment in the near field and/or far field. For example, tungsten filament lamps have a low electrical to optical efficiency and, thus, require large amounts of electrical power to generate high intensity optical energy, which results in large quantities of thermal energy. Furthermore, high power tungsten lamps have a low lamp lifetime, usually operating for about 500 hours. Xenon arc lamps provide optical energy with higher intensity than metal halide lamps, but have a low luminous efficiency and low lamp life time (around 500 hours). Furthermore, traditional light sources such as arc lamps, for example, when used as a light source for a less than spherical illumination region, are optically inefficient.

Accordingly, there is a long-felt need to for radiation devices or apparatus that can provide a desired wavelength or wavelengths of electromagnetic radiation, at a desired radiant power output, in an efficient manner such that the power consumption is both practical and the heat generated to the surrounding environment is minimized.

SUMMARY OF THE INVENTION

Therefore, it is an objective of the present disclosure to provide a robust, flexible, multifunctional radiation delivery system that is also cost-effective to manufacture and operate. It is a further objective to provide an electromagnetic radiation delivery system that operates at low voltage with no need for expensive and dangerous voltages required for the mercury based systems. Another objective of the present disclosure is to provide a system with fast start-up times that can be pulsed on and off effectively. A further objective of the present disclosure is to provide a system that produces high intensity, spatially-uniform, light in a reduced package size that does not significantly heat the surrounding environment and is small and compact enough to be mobile and transportable in a typical office or hospital environment. Yet another objective of the present disclosure is to provide a multifunctional radiation delivery system with an automated control system for controlling the power supplied to a target area. Yet another objective of the present disclosure is to provide a multifunctional radiation delivery system with additional therapeutic components making it more useful in a therapeutic setting.

One aspect of the present disclosure is to provide an apparatus for delivering electromagnetic radiation to a stationary target. The apparatus comprises a housing having a front face, a primary radiation source for providing electromagnetic radiation to a target portion of the stationary target, and a heat sink positioned within the housing, wherein the primary radiation source comprises an array of light-emitting diodes, wherein the array of light-emitting diodes comprises at least one light-emitting diode, and wherein electromagnetic radiation emitted by the primary radiation source is emitted through the front face; a moveable arm having a first end adjustably interconnected to the housing, and having a second end, wherein the housing is one or more of rotatable, slidable, and translatable relative to the moveable arm; a body adjustably interconnected to the second end of the moveable arm, wherein the body is one or more of rotatable, slidable, and translatable relative to the moveable arm; a movement device; a positioning system, comprising a targeting device and a distance-setting device, wherein the targeting device comprises a reticle; a measuring device for collecting measurement data from the target portion of the stationary target; and a control system for setting the measurement data from the target portion of the stationary target to a predetermined value by adjusting at least one of a radiation power and a target distance, wherein the target distance is the distance between the front face of the housing and the target portion of the stationary object. In some embodiments, the electromagnetic radiation has a wavelength of between about 800 nanometers and about 950 nanometers. In some embodiments, the radiation power is between about 1 watt and about 5,000 watts. In some embodiments, at least one light-emitting diode provides electromagnetic radiation with a wavelength of about 850 nanometers. In some embodiments, the apparatus further comprises a heat spreader positioned between the primary radiation source and the heat sink. In some embodiments, the apparatus further comprises a secondary radiation source. In some embodiments, the apparatus further comprises a filter. In some embodiments, the apparatus further comprises a focusing system. In some embodiments, the apparatus further comprises a power density equalizer. In some embodiments, the positioning system further comprises a means for locking and unlocking the target distance.

Another aspect of the present disclosure is to provide an apparatus for delivering electromagnetic radiation to a stationary target. The apparatus comprises a housing; a body; a movement device; a positioning system comprising a targeting device and a distance-setting device, wherein the targeting device comprises a reticle; a measuring device for collecting measurement data from the target portion of the stationary target; and a control system for setting the measurement data from the target portion of the stationary target to a predetermined value by adjusting at least one of a radiation power and a target distance, wherein the target distance is the distance between the front face of the housing and the target portion of the stationary object. The housing comprises a front face; a primary radiation source comprising an array of light-emitting diodes, wherein the array of light-emitting diodes comprises at least one light-emitting diode, and wherein the primary radiation source provides electromagnetic radiation with a wavelength of between about 800 nanometers and about 950 nanometers and a power of between about 1 watt and about 5,000 watts; a secondary radiation source comprising a light source that is not a light-emitting diode; a heat sink, wherein the primary radiation source and the secondary radiation source are both in contact with the heat sink; a heat spreader in contact with the heat sink; a filter positioned adjacent to one or more of the primary radiation source and the secondary radiation source; a focusing system positioned adjacent to the filter; and a power density equalizer positioned adjacent to the focusing system. In some embodiments, the apparatus further comprises a moveable arm having a first end adjustably interconnected to the housing, and having a second end adjustably interconnected to the body, wherein the housing and the body are each one or more of rotatable, slidable, and translatable relative to the moveable arm.

A further aspect of the present disclosure is to provide a method for thermally ablating a target tissue of a patient. The method comprises injecting a mixture comprising gold nanoparticles into the target tissue, wherein the nanoparticles have a length of between about 30 nanometers and about 60 nanometers and a width of between about 10 nanometers and about 14 nanometers; providing a device; moving a moveable arm and a housing of the device to enable moving of a front face of the housing relative to the target tissue of the patient; targeting electromagnetic radiation provided by a primary radiation source of the device on the target tissue of the patient using a positioning system of the device; setting the distance between the front face of the housing and the target tissue of the patient to a target distance; radiating the target tissue; measuring a variable of the target tissue; and setting the variable to a predetermined value by adjusting at least one of the target distance and a power of the electromagnetic radiation provided by the primary radiation source, such that a temperature of the target tissue is raised by at least 5 degrees Celsius. The device comprises a housing, comprising a front face, a heat sink, and a primary radiation source comprising an array of light-emitting diodes, wherein each array of light-emitting diodes comprises at least one light-emitting diode, and wherein the primary radiation source provides electromagnetic radiation with a wavelength of about 950 nanometers, and a power of between about 1 watt and about 100 watts; a moveable arm, comprising a first end and a second end; a body; a movement device; a positioning system, comprising a targeting device and a distance-setting device, wherein the targeting device comprises a reticle; a measuring device for collecting measurement data from the target portion of the target tissue; and a control system for setting the measurement data from the target portion of the target tissue to a predetermined value by adjusting at least one of a target distance and the power of the electromagnetic radiation provided by the primary radiation source, wherein the target distance is the distance between the front face of the housing and the target portion of the stationary target, wherein the housing is adjustably interconnected to the first end of the moveable arm and the body is adjustably interconnected to the second end of the moveable arm, and wherein the housing and the body are each one or more of rotatable, slidable, and translatable relative to the moveable arm.

The preceding is a simplified summary to provide an initial understanding of the aspects, embodiments and configurations disclosed herein. This summary is neither an extensive nor exhaustive overview of the aspects, embodiments, or configurations. It is intended neither to identify key or critical elements, nor to delineate the scope of the aspects, embodiments, or configurations but to present selected concepts in a simplified form as an introduction to the more detailed description presented below. As will be appreciated, other aspects, embodiments, and configurations are possible utilizing, alone or in combination, at least one of the features set forth above or described in detail below.

BRIEF DESCRIPTION OF THE DRAWINGS

The accompanying drawings are incorporated into and form a part of the specification to illustrate examples of how the aspects, embodiments, or configurations can be made and used and are not to be construed as limiting the aspects, embodiments, or configurations to only the illustrated and described examples. Further features and advantages will become apparent from the following, more detailed, description of the various aspects, embodiments, or configurations.

Figure 1:
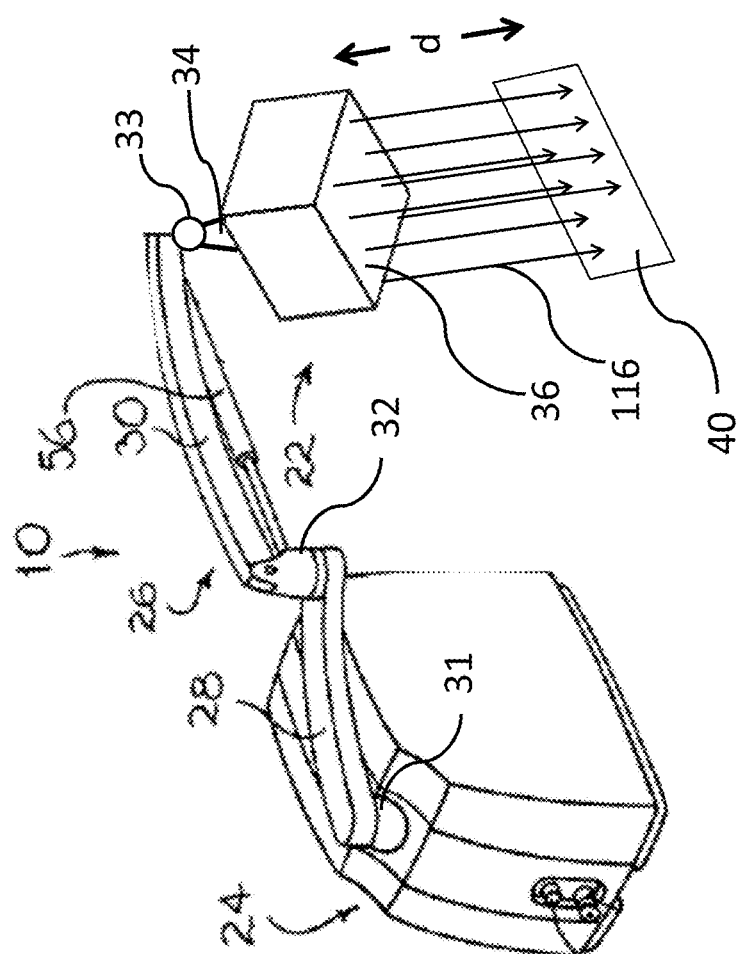
FIG. 1 illustrates one embodiment of an apparatus for delivering electromagnetic energy to a target surface, of the present disclosure.

To assist in the understanding of the embodiments of the present invention the following list of components and associated numbering found in the drawings is provided herein:

| #   | component                                     |
|-----|-----------------------------------------------|
| 10  | apparatus for delivering electromagnetic energy |
| 22  | housing                                       |
| 24  | body                                          |
| 26  | moveable arm                                  |
| 28  | first length                                  |
| 30  | second length                                 |
| 31  | first joint                                   |
| 32  | second joint                                  |
| 33  | third joint                                   |
| 34  | connecting means                              |
| 36  | front face                                    |
| 40  | target surface                                |
| 56  | means for moving                              |
| 100 | primary radiation source                      |
| 102 | additional radiation source                   |
| 104 | power source                                  |
| 106 | user interface                                |
| 108 | positioning system                            |
| 110 | measuring device                              |
| 112 | heat sink                                     |
| 114 | filter                                        |
| 116 | electromagnetic radiation                     |
| 118 | power density equalizer                       |
| 120 | focusing system                               |

It should be understood that the drawings are not necessarily to scale, and various dimensions may be altered. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION

The following detailed description illustrates the invention by way of example and not by way of limitation. This description will clearly enable one skilled in the art to make and use the invention.

The present disclosure relates to methods, apparatus, and devices for the controlled application of electromagnetic radiation to a target. Potential uses for embodiments of the present disclosure include, but are not limited to, surface plasmon resonance imaging and therapies, tissue illumination or fluorescence, biological illumination such as to aid in the in vitro growth of cultures, curing systems (e.g. plastics, paint, etc.), plastic molding operations, medical treatments and therapies, and photodynamic therapies. Additional specific medical applications include, but are not limited to, stimulation of new cell growth in wounds, the eradication of pathogenic organisms, and the activation of photosensitive chemicals for the treatment of skin or other cancers. In particular, as described in PCT Application Publication No. WO 2013/095736 and U.S. Patent Application Publication No. 2008/0160090, both of which are incorporated herein by reference, cancer therapies are disclosed comprising the use of gold nanoparticles for targeted thermal or mechanical ablation of human tumors, wherein the nanoparticles are heated by an external energy source.

To reduce the need to provide extensive disclosure in this application, but to provide adequate written description of the various devices and methods encompassed by the numerous embodiments of the present disclosure, various patents are incorporated herein in their entireties this reference. It will be appreciated by one of skill in the art that various structural elements can be combined with the present structure of the present disclosure to achieve various desired purposes. PCT Patent Application Publication No. WO 2012/057819 describes a light emitting diode projector comprising a collection of optics which provides a homogenized LED output whose intensity is highly uniform. U.S. Patent Application Publication No. 2005/0055015 discloses a laser delivery device incorporating a plurality of laser source optical fibers. U.S. Pat. No. 7,488,102 discloses a white-light optical system that provides spatially uniform high intensity light over a target area. PCT Patent Application Publication No. WO 2013/165499 describes an integrated targeting device to estimate the position of a target comprising an imaging camera. PCT Patent Application Publication No. WO 2007/149221 describes a laser diode based system for producing infrared radiation of a very specific wavelength for purposes of irradiating objects in a variety of fields. U.S. Patent Application Publication No. 2007/0225778 describes an LED array which is selectable and can be aimed to match the size and shape of a target area. U.S. Pat. No. 7,815,668 discloses medical treatment methods and devices that combine light and hyperbaric therapies. U.S. Patent Application Publication No. 2007/0225778 discloses an apparatus for adjusting the size and shape of LED light to match the size and shape of a target. U.S. Pat. No. 7,887,533 discloses a device for the treatment of mammalian tissues. U.S. Patent Application Publication No. 2002/0128695 discloses an apparatus for photodynamic therapy of skin disorders. Each of these U.S. patent documents is incorporated herein by reference in their entirety.

The following additional U.S. patents are also incorporated herein by reference in their entirety: U.S. Pat. Nos. 8,278,841, 7,276,058, 6,201,425, 4,822,335, 6,645,230, 5,944,748, 6,955,684, 7,125,416, 5,358,503, 8,480,720, 6,354,297, 8,328,796, 5,300,097, 7,220,254, 5,728,090, 7,118,563, 6,866,678, 7,517,101, 7,422,598, 8,486,056, 7,156,865, 8,481,982, 8,134,132, 7,189,983, 6,955,684 and 5,042,494. The following additional U.S. patent publications are also incorporated herein by reference in their entirety: U.S. Patent Application Publication Nos. 2012/0041523, 2004/0093043, 2006/0287696, 2009/0088824, 2010/

0286674, 2007/0032843, 2012/0123507, and 2012/0150044. Also incorporated herein by reference in their entirety are European Patent Application Publication Nos. 2149743 and 1645307 and PCT Patent Application Publication Nos. WO 1993/021842 and WO 2008/125772.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, a "movement device" is any means for moving associated with a moveable arm and a housing, to enable moving of a front face of the housing relative to a stationary target. By way of non-limiting example, a movement device may be a handle which may be manually adjusted by a user, or a motorized system.

As used herein, a "targeting device" is any means for targeting electromagnetic radiation on a target portion of a stationary target. By way of non-limiting example, a targeting device may be a reticle.

As used herein, a "distance-setting device" is any means for setting a distance between a front face of a housing and a target portion of a stationary target to a desired distance. By way of non-limiting example, a distance-setting device may be a laser range finder.

As used herein, a "measuring device" is any means for measuring a variable of a target portion of a stationary target. By way of non-limiting example, a measuring device may be an optical camera, an infrared camera, a computed tomography (CT) device, a magnetic resonance imaging (MRI) device, a fluoroscopic imaging device, a positron emission tomography (PET) device, or an ultrasound imaging (US) device. By way of non-limiting example, the variable measured by the measuring device may be heat emitted, temperature, absorptivity, color, luminosity, photosensitivity, reflectivity, refractive index, radiation scattering, or radiation transmittance.

An aspect of the present disclosure is an apparatus for delivering electromagnetic radiation to a stationary target comprising a housing with a front face, and a primary radiation source and a heat sink positioned within the housing, wherein the primary radiation source provides a power emitted, a moveable arm comprising a first end and a second end with a length spanning between the first end and the second end, and a body, wherein the housing is adjustably connected to the first end of the moveable arm, and the body is adjustably connected to the second end of the moveable arm. The apparatus also comprises a movement device, a positioning system comprising a targeting device and a distance-setting device, a measuring device, and a control system for controlling the metric to a set-point, by at least one of adjusting the power emitted and the target distance.

In some embodiments of the present disclosure, the primary radiation source may be at least one light emitting diode (LED). In some embodiments of the present disclosure the at least one LED may be constructed of at least one of gallium arsenide (GaAs), aluminum gallium arsenide (AlGaAs), gallium arsenide phosphide (GaAsP), aluminum gallium indium phosphide (AlGaInP), gallium (III) phosphide (GaP), indium gallium nitride (InGaN), gallium (III) nitride (GaN), zinc selenide (ZnSe), silicon carbide (SiC), silicon (Si) and combinations thereof. In further embodiments of the present disclosure, the at least one LED may be an ultraviolet LED, blue LED, white light LED, multi-color white LED, monochromatic LED, dichromatic LED, trichromatic LED, multichromatic LED, phosphor-based LED, zinc selenide LED, and combinations thereof. In still other embodiments of the present disclosure, the at least one LED may be an organic light-emitting diode or a quantum dot light-emitting diode.

In some embodiments of the present disclosure, the at least one LED may be a miniature LED that may comprise a power consumption of 40 mW or less at a voltage of about 2 volts. In some embodiments of the present disclosure, the at least one LED may comprise a power consumption ranging from about 20 mW to about 200 mW at a voltage corresponding to a range from about 0.5 volts to about 10 volts. In still further embodiments, the at least one LED may comprise a mid-range LED with an operating current up to about 100 mA. In still further embodiments of the present disclosure, the at least one LED may comprise a high-power LED with an operating current from about 100 mA to about 5 A and radiation power up to 5000 W.

In some embodiments of the present disclosure, the at least one LED may produce a power from about 0.1 W to about 30,000 W. In further embodiments of the present disclosure the at least one LED may produce a power from about 0.1 W to about 10,000 W. In still further embodiments of the present disclosure the at least one LED may produce a power from about 0.1 W to about 5,000 W. In still further embodiments of the present disclosure the at least one LED may produce a power from about 1.0 W to about 5,000 W.

In some embodiments of the present disclosure, the primary radiation source may comprise an array of LEDs from one LED up to about 10,000 LEDs. In some embodiments of the present disclosure, the primary radiation source may comprise an array of LEDs from one LED up to about 1,000 LEDs. In some further embodiments of the present disclosure, the primary radiation source may comprise an array of LEDs from one LED up to about 500 LEDs. In still further embodiments of the present disclosure, the primary radiation source may comprise an array of LEDs from one LED up to about 100 LEDs.

In some embodiments of the present disclosure, the primary radiation source may comprise an LED die or a closely packed die array or matrix of die arrays. In some further embodiments of the present disclosure, the primary radiation source may comprise an LED array arranged in a near flat circular plane, or in a hexagonal arrangement, or any other suitable geometric shape or arrangement. The LEDs of an array may be arranged in a single flat plane, or on a curved surface such as a concave surface or convex surface.

In some embodiments of the present disclosure, the primary radiation source may be at least one laser based radiation emitting source. In some embodiments of the present disclosure the at least one laser based radiation emitting source may include but is not limited to at least one of diode, ion, dye, Ti:sapphire, Alexandrite, solid state and the like. A variety of different host materials can be utilized with the solid state lasers including but not limited to, YAG, YVO4 or YSGG doped with rare earth elements such as Nd, Yb, Er, Ho, Tm and the like.

In some embodiments of the present disclosure, the primary radiation source may emit electromagnetic radiation ranging in wavelength from about 400 nm to about 1200 nm. In further embodiments of the present disclosure, the primary radiation source may emit light ranging in wavelength from about 700 nm to about 1000 nm. In still further embodiments of the present disclosure, the primary radiation source may emit light ranging in wavelength from about 800 nm to about 950 nm.

In some embodiments of the present disclosure, the primary radiation source may emit a distribution of light. Such a distribution may comprise a normal distribution of wavelengths, a bimodal distribution, or any other non-normal distribution. In other embodiments of the present disclosure, the primary radiation source may emit a distribution of electromagnetic radiation ranging in wavelength from about 400 nm to about 1200 nm. In further embodiments of the present disclosure, the primary radiation source may emit a distribution of electromagnetic radiation ranging in wavelength from about 700 nm to about 1000 nm. In still further embodiments of the present disclosure, the primary radiation source may emit a distribution of electromagnetic radiation ranging in wavelength from about 800 nm to about 950 nm.

In some embodiments of the present disclosure, the primary radiation source may emit from 1 to 10 wavelengths of electromagnetic radiation. In further embodiments of the present disclosure, the primary radiation source may emit from 1 to 5 wavelengths of electromagnetic radiation. In still further embodiments of the present disclosure, the primary radiation source may emit from 1 to 3 wavelengths of electromagnetic radiation. In some embodiments of the present disclosure, the primary radiation source may emit one wavelength of electromagnetic radiation. In still further embodiments of the present disclosure, the primary radiation source may emit one wavelength of electromagnetic radiation which is one of 830 nm, 831 nm, 832 nm, 833 nm, 834 nm, 835 nm, 836 nm, 837 nm, 838 nm, 839 nm, 840 nm, 841 nm, 842 nm, 843 nm, 844 nm, 845 nm, 846 nm, 847 nm, 848 nm, 849 nm, 850 nm, 851 nm, 852 nm, 853 nm, 854 nm, 855 nm, 856 nm, 857 nm, 858 nm, 859 nm, 860 nm, 861 nm, 862 nm, 863 nm, 864 nm, 865 nm, 866 nm, 867 nm, 868 nm, 869 nm, or 870 nm.

In some embodiments of the present disclosure, the LEDs of an LED array may be adapted to emit the same wavelength, or at least two different wavelengths. In some embodiments of the present disclosure, an LED array may comprise a plurality of sub-arrays each adapted to emit a different wave length. For example, one sub-array of LEDs may be adapted to emit near-infrared light (e.g., light having a wavelength within the range from about 1000 to 800 nanometers), one sub-array of LEDs may be adapted to emit visible light (e.g., light having a wavelength within the range from about 800 to 400 nanometers), and another sub-array of LEDs may be adapted to emit ultraviolet light (e.g., light having a wave length within the range from about 400 to 200 nanometers). Other combinations and numbers of wavelengths of light may be employed, as may be other wavelength ranges. The LEDs employed within an LED array may comprise any conventional light emitting diodes adapted to emit light of the desired wavelength/frequency.

In some embodiments of the present disclosure, the apparatus for delivering electromagnetic radiation may include an LED array having a plurality of LEDs configured in a desired arrangement; e.g. circular, oval, hexagonal, etc. The LED array may be divided into more than one sub-array of LEDs, wherein each sub-array emits a different wavelength, thereby forming multiple controllable LED channels. In some further embodiments of the present disclosure, four wavelengths may be emitted by four LED sub-arrays, wherein the wavelengths are 848 nm, 849 nm, 850 nm, and 851 nm, although other wavelengths may be employed.

In some embodiments of the present disclosure, each LED sub-array of the primary radiation source may represent an isolated circuit of a plurality of LEDs, which may be arranged uniformly interspersed among the other LED sub-arrays, rather than having all LED's of the same wavelength grouped together.

In some embodiments of the present disclosure the primary radiation source may be physically connected to a heat sink, wherein the heat sink comprises a high thermal conductive material. The heat sink may be cooled by a fan or air, or forced water, or other forced, recirculating cooling medium. In further embodiments of the present disclosure, an optional heat spreader may be positioned between the heat sink and the primary radiation source. The heat spreader may be thermally attached to the primary radiation source to pull thermal energy away from the primary radiation source and disperse the thermal energy away from the primary radiation source. Increased thermal dissipation provides for increased electric efficiency within the primary radiation source. In an alternative embodiment of the present disclosure, the heat spreader material may include diamond. Diamond has a high thermal conductivity and thus permits higher operating currents to be used without increasing the temperature of primary radiation source. In an alternative embodiment of the present disclosure, the heat spreader material may include any material with a high conductivity, such as, but not limited to copper, aluminum, etc. The heat spreader may be thermally attached to the thermal dissipater and/or the heat sink.

In some embodiments of the present disclosure, the apparatus for delivering electromagnetic radiation may comprise at least one additional radiation source. In some embodiments of the present disclosure, the at least one additional radiation source may comprise at least one mercury arc lamp, xenon arc lamp, metal halide arc lamp, quartz infrared lamp, tungsten filament lamp, laser, LED array, and combinations thereof.

In some embodiments of the present disclosure, the at least one additional radiation source may produce a power, or emit a power from about 0.1 W to about 30,000 W. In further embodiments of the present disclosure the at least one additional radiation source may produce a power from about 0.1 W to about 10,000 W. In still further embodiments of the present disclosure the at least one additional radiation source may produce a power from about 0.1 W to about 5,000 W. As used herein, the term "power emitted" refers to the amount of radiation power emitted by the various radiation sources. This is not the same as the power provided to the radiation sources. As one skilled in the art will recognize, any radiation source will have a certain energy efficiency that relates to the electrical power provided to the radiation source and the amount of radiant energy emitted by the radiation source. The ratio of the radiant energy emitted to the electrical power provided is always less than one. As used herein, the term "power transferred" refers to the radiant energy per unit time provided to the target surface.

As there will always be energy losses to the surrounding environment, the "power transferred" will always be less than the radiant energy emitted by the radiation source. The power transferred can be measured in terms of the total power transferred, e.g. about 0.1 W to about 5,000 W, or it can be quantified in terms of power per unit surface area of the target area. Typical target surface will range from less than 1 $cm^2$ up to about 1000 $cm^2$. In still further embodiments of the present disclosure, the target surface area may be as large as 1000 $cm^2$, 10,000 $cm^2$, or 100,000 $cm^2$.

In some embodiments of the present disclosure, the at least one additional radiation source may emit electromagnetic radiation ranging in wavelength from about 400 nm to about 1200 nm. In further embodiments of the present disclosure, the at least one additional radiation source may emit light ranging in wavelength from about 700 nm to about 1000 nm. In still further embodiments of the present disclosure, the at least one additional radiation source may emit light ranging in wavelength from about 800 nm to about 950 nm.

In some embodiments of the present disclosure, the at least one additional radiation source may emit a distribution of light. Such a distribution may comprise a normal distribution of wavelengths, a bimodal distribution, or any other non-normal distribution. In other embodiments of the present disclosure, the at least one additional radiation source may emit a distribution of electromagnetic radiation ranging in wavelength from about 400 nm to about 1200 nm. In further embodiments of the present disclosure, the at least one additional radiation source may emit a distribution of electromagnetic radiation ranging in wavelength from about 700 nm to about 1000 nm. In still further embodiments of the present disclosure, the at least one additional radiation source may emit a distribution of electromagnetic radiation ranging in wavelength from about 800 nm to about 950 nm.

In some embodiments of the present disclosure the at least one additional radiation source may be physically connected to a heat sink, wherein the heat sink comprises a high thermal conductive material. The heat sink may be cooled by a fan or other air or water supply. In further embodiments of the present disclosure, the at least one additional radiation source may be associated with an optional heat spreader which may be positioned between the heat sink and the at least one additional radiation source. In some embodiments of the present disclosure, the primary radiation source and the at least one additional radiation source may utilize the same heat sink. In further embodiments of the present disclosure, the primary radiation source and the at least one additional radiation source may each have its own independent and distinct heat sink. In some embodiments of the present disclosure, the primary radiation source and the at least one additional radiation source may utilize the same heat spreader. In further embodiments of the present disclosure, the primary radiation source and the at least one additional radiation source may each have its own independent and distinct heat spreader.

In some embodiments of the present disclosure, the primary radiation source and at least one secondary radiation source and their corresponding heat sink(s) and optional heat spreader(s) may be physically located in a housing. The front face of the housing may comprise a planar surface from which the electromagnetic radiation is emitted. The radiation may be emitted at an angle orthogonal to the surface of the front face, or alternatively the radiation may be emitted at some angle other than 90 degrees. Alternatively, the front face may comprise a non-planar surface, for example, but not limited to, convex or concave surfaces. It should be clear to one of ordinary skill in the art, that the physical dimensions of the housing will depend on the specific design specifications and size of the heat source, heat sink, optional heat spreader, as well as any other related components to be located within the housing, some of which will discussed in more detail below. However, a primary feature of the housing of the present disclosure is that the housing is of sufficient size to enable movement of the housing relative to the target surface. More specifically, when operating the apparatus for delivering electromagnetic radiation, one must be able to position the front face of the housing at a distance from the target surface that will provide radiation in the desired pattern, power emitted, and energy density delivered to the target surface.

In some embodiments of the present disclosure, the apparatus for delivering electromagnetic radiation may further comprise at least one filter, which may be positioned substantially parallel to the surface emitting the radiation, so as to adjust a feature of the radiation being emitted. In some embodiments of the present disclosure, a filter may comprise at least one of an absorptive filter, a dichroic filter, a monochromatic filter, an infrared filter, an ultraviolet filter, a neutral density filter, a longpass filter, a bandpass filter, a shortpass filter, a guided-mod resonance filter, a polarizer, any other suitable filter, and combinations thereof. In some further embodiments of the present disclosure, at least one filter may be placed over at least one of the primary radiation source, the at least one additional radiation source, and combinations thereof. In still further embodiments of the present disclosure, at least one filter may be placed over at least one specific LED array or sub-array. In some embodiments, at least one filter may be used to adjust at least one of the wavelength of radiation that reaches the target surface, the distribution of wavelengths that reaches the target surface, the power density that reaches the target surface, and combinations thereof.

In some embodiments, the apparatus for delivering electromagnetic radiation may further comprise at least one mechanical shutter which may be placed substantially parallel to and near the surface from which the radiation is emitted. A mechanical shutter may provide the ability to pulse the radiation emitting, especially for any radiation sources that are not LEDs.

In some embodiments of the present disclosure, the apparatus for delivering electromagnetic radiation may further comprise at least one focusing system which may be placed substantially parallel to and near the surface from which the radiation is emitted. Such a focusing system may include, for example, at least one appropriately selected optical component, such as a lens. A focusing system may focus the radiation emitted apparatus onto a specific portion of the target being radiated. A focusing system may control a direction in which the radiation emitted by each of the plurality of light sources propagates so that the light travels towards the surface target or a portion thereof. In some embodiments of the present disclosure, a focusing system may comprise at least one of a totally internal reflecting lens, a refractive lens, and combinations thereof.

In some embodiments of the present disclosure, the apparatus for delivering electromagnetic radiation may further comprise at least one power density equalizer. Examples of power equalizers that may be used in some embodiments of the present disclosure are disclosed in PCT Patent Application Publication No. WO 2012/057819 and U.S. Pat. No. 7,488,102 which are incorporated herein by reference in their entirety. The purpose of the power density equalizer is to insure that the power of the radiation emitted by the apparatus is constant across the target area. In some embodiments of the present disclosure, the electromagnetic radiation radiating the target area varies in power density (W/cm$^2$) by less than ±15% relative to the average power density supplied across the entire surface area of the target. In some embodiments of the present disclosure, the electromagnetic radiation radiating the target area varies in power density (W/cm$^2$) by less than ±10% relative to the average power density supplied across the entire surface area of the target. In some embodiments of the present disclosure, the electromagnetic radiation radiating the target area varies in power density (W/cm$^2$) by less than ±5% relative to the average power density supplied across the entire surface area of the target. In some embodiments of the present disclosure, the electromagnetic radiation radiating the target area varies in power density (W/cm$^2$) by less than ±1% relative to the average power density supplied across the entire surface area of the target.

In some embodiments of the present disclosure, a measuring device may comprise at least one optical camera. Target surface metrics that may be measured in some embodiments of the present disclosure, include, but are not limited to, heat emitted, temperature, absorptivity, color, luminosity, photosensitivity, reflectivity, refractive index, radiation scattering, radiation transmittance, and combinations thereof. In some embodiments of the present disclosure, the surface metric measured may be at least one of heat emitted, temperature, and combinations thereof. In some further embodiments of the present disclosure, a measuring device may be an infrared camera. In still further embodiments of the present disclosure, a measuring device may further comprise a separate electromagnetic radiation source specific to a detector of the measuring device. For example, a separate electromagnetic radiation source may be used that emits radiation in at least one wavelength other than the wavelengths emitted by the primary radiation source or the at least one additional radiation source, wherein a detector is selected to detect just the at least one wavelength emitted by the separate electromagnetic radiation source, or other specific wavelengths associated with the separate source.

In some embodiments of the present disclosure, the measuring device may comprise at least one of computed tomography, magnetic resonance imaging, fluoroscopic imaging, positron emission tomography, and ultrasound imaging.

In some embodiments of the present disclosure, at least one of the primary radiation source, the at least one additional radiation source, and the separate radiation source is arranged in a circular arrangement about the measuring device, wherein the measuring device is positioned substantially near the center of the circular arrangement. In some further embodiments of the present disclosure, at least one of the primary radiation source, the at least one additional radiation source, and the separate radiation source is arranged in a hexagonal arrangement about the measuring device, wherein the measuring device is positioned substantially near the center of the hexagonal arrangement. In still further embodiments of the present disclosure, the measuring device is positioned substantially adjacent to a side of an array of electromagnetic radiation sources, wherein the array may be circular, hexagonal, or any other suitable geometric shape.

In some embodiments of the present disclosure, a positioning system may comprise at least one of a visual light system, a GPS system, a laser rangefinder, a laser designator, an optical reflectance system, and combinations thereof. In some further embodiments of the present disclosure, the positioning system may comprise a non-invasive dynamic reference frame and/or fiducial marker, and sensors placed on the target surface, as described in U.S. Pat. Nos. 7,840, 253, 7,835,778, and 7,763,035 which are incorporated herein by reference. In still further embodiments, a positioning system may comprise cross-hairs of visible light, which are manually positioned on the target surface. A positioning system of the present disclosure insures that the front face of the radiation delivery device is correctly positioned relative to the target surface in three-dimensional space. In some embodiments of the present disclosure, the positioning system may insure that the front face of the radiation delivery device is substantially parallel to the target surface. In still further embodiments of the present disclosure, the positioning system may insure that the front face of the radiation delivery system is a specific distance away from the target surface, or within a range of distances away from the target surface. In still further embodiments of the present disclosure, the positioning system may comprise at least one laser for generating at least one light beam on a target area (e.g., at least one visible light beam). The at least one light beam may be used, for example, to identify the outermost area irradiated by the electromagnetic radiation sources. Other suitable targeting mechanisms may include, for example, crosshairs, viewfinders, physical place holders, etc. An example of a physical place holder is a telescoping ruler which allows the user to manually place the housing within a desired distance from the target surface. Another example is a set of calipers associated with the device to manually adjust the distance between the housing and the target surface. It should be known to one of ordinary skill in the art, that other physical place holders can be envisioned for manually adjusting the distance between the housing and the target surface, and such embodiments are considered within the scope of the present disclosure.

FIG. 1 illustrates an apparatus for delivering electromagnetic energy 10 in accordance with the present disclosure, wherein a front face 36 of a housing 22 has been positioned at a desired distance d from a target surface 40, which is being radiated with electromagnetic radiation. FIG. 1 illustrates one possible arrangement, within the scope of this disclosure, of a moveable arm, which enables a wide range of movement options for the housing 22 relative to the target surface 40. The length of the moveable arm is divided into a first length 28 and a second length 30, which connect a body 24 to the housing 22. The distal end of the first length 28 terminates in a second joint 32, which attaches to the proximal end of the second length 30. The proximal end of the first length 28 is pivotally coupled to a first joint 31, which attaches to the body 24 for pivotal movement relative thereto. The first length 28 may rotate a full 360 degrees around a vertical axis extending through the body 24. In addition, the second joint 32 located at the body 24 may also rotate upward out of the horizontal plane, up to 180 degrees. However, it should be understood that the first length's 28 degrees of rotational movement can have other values without departing from the scope of the present disclosure. The proximal end of the second length 30 attaches to the distal end of the first length 28 at the second joint 32. This second joint 32 may comprise any articulating means known to one of ordinary skill in the art to allow the second length 30 to rotate around the joint to any desirable position within three-dimensional space. For example, the second length 30 may rotate a full 360 degrees in a plane around the second joint 32 at the distal end of the first length 28. The second length 30 may also rotate relative to the first length 28 in a vertical plane.

It should, however, be understood that the second length 30 horizontal and vertical rotation ranges and the first length 28 horizontal and vertical rotation ranges, as well as their general movement within three-dimensional space, can be varied to suit the particular design and functional needs of a particular apparatus. Similarly, the specific lengths of the first and second lengths may have any desired specific values, as required by a specific apparatus.

In some embodiments of the present disclosure, a moveable arm 26 may include a weight compensating assembly or means mechanically coupled to a portion of the moveable arm 26 for at least partially compensating for the weight of the housing 22. A movement device is also shown in FIG. 1, which may, for example, comprise a means for raising the second length 30 in a vertical direction. The moveable arm 26 may also include a universal-type mechanical coupling or swivel extending between the second length 30 and substantially adjacent the distal end of the second length 30 and the housing 22 for mechanically coupling the latter and allowing the housing 22 to pivot and rotate relative to the second length 30. The moveable arm 26 may also include a releasable locking assembly or means for releasably locking the housing 22 in an operational position relative to the second length 30 and the target surface 40. The swivel and the locking means may take any suitable form without departing from the scope of the present disclosure. In one embodiment, a third joint 33 and a connecting means 34 at the distal end of the second length 30 may include a swivel ball mounted within a corresponding swivel socket so as to form a ball and socket-type joint, to allow a maximum amount of movement of the housing 22 in three dimensions. The mechanical coupling may be a universal-type. Although the swivel range may have a value of approximately 115 degrees in one plane, it should be understood that the swivel range also acts across multiple planes wherein the swivel range for each plane can be the same or different values. Additionally, the swivel ranges can have other values without departing from the scope of the present disclosure. The moveable arm mechanical coupling may also allow the housing 22 to rotate relative to a head rotational axis extending substantially perpendicular to the longitudinal axis of the second length 30. Thus, the mechanical coupling may allow the housing 22 to spin on one axis, permitting the housing 22 to be orientated to any angle in relation to the body 24, as well as second length 30. Most importantly, these features allow the front face 36 to be set to any orientation relative to the target surface 40 being radiated by the apparatus 10. A releasable locking means may include a means for increasing the friction between the joints connecting the components; e.g. body 24, first length 28, second length 30, and housing 22. In some embodiments of the present disclosure, the apparatus for delivering electromagnetic radiation may not include an arm.

It will be obvious to one of ordinary skill in the art, that the body 24 may comprise any suitable dimensions, such as length, width, height, and volume, to suit the needs of a specific embodiment of the current disclosure. For example, the dimensions of the body may be selected to house at least one of the power supply and the electronic components associated with the movement device, the positioning system, the measuring device, the control system, and combinations thereof.

In some embodiments of the present disclosure, the movement device may comprise a handle which the user manually adjusts, for example, to place the cross-hairs of a positioning system on the target surface. To facilitate useful movement, the moveable arm may comprise at least one joint, wherein each joint provides sufficient friction such that once the arm and housing are manually positioned in the desired location relative to the target surface, the housing and arm remain in that location until moved by the user.

In some embodiments of the present disclosure, the movement device may comprise a motorized system. In such embodiments of the present disclosure, the moveable arm is essentially a robotic arm, wherein movement of the housing relative to the target surface is controlled by rotational movement around at least one axis of the joints (31, 32, 33 of FIG. 1). In some embodiments of the present disclosure, the moveable arm comprises at least one rotary joint, pivot joint, hinge joint, ball-and-socket joint, and cylindrical joints. The moveable arm of the present disclosure may be a robotic arm selected from the group consisting of a Cartesian robot, a cylindrical robot, a spherical robot, a SCARA robot, an articulated robot, a parallel robot, an anthropomorphic robot, and any other suitable robotic arm known to one of ordinary skill in the art. In some embodiments of the present disclosure, the movement device may also comprise a means for fixing or locking the moveable arm in a desired position.

In some embodiments of the present disclosure, the moveable arm of the multifunctional radiation delivery apparatus may comprise a robotic arm, such that the robotic arm enables automated movement of the housing relative to the target surface. Therefore, to enable automated movement of the moveable arm, another feature of the present disclosure is a control system, wherein the control system manipulates, among other things, the movement of a robotic arm to match a set-point value defined by the user. In some embodiments of the present disclosure, a radiation delivery apparatus may further comprise, for example, at least one user interface comprising at least one of a desktop computer, a laptop computer, a microcontroller, a personal digital assistant (PDA), a keyboard, a computer screen, and any other suitable interface. Further features of a user interface may comprise a central processing unit, and a data storage means (e.g. RAM, ROM, etc.). The data storage means may also store software related to the operation of the various features of the radiation delivery apparatus; e.g. movement device, positioning system, measuring device, and the control system.

By way of example, in some embodiments of the present disclosure, a user may interface with the apparatus for delivering electromagnetic radiation to a stationary target by entering a set-point value for a variable at a user interface. Entering a set-point may be performed using a keyboard interactively connected to a display screen. A variable entered may, for example, be at least one of a power density and distance between the front face of the housing and the target surface. In some embodiments of the present disclosure, a desired set-point distance may range from 0.1 cm to 3 meters. In some embodiments of the present disclosure, a desired set-point distance may range from 0.1 cm to 100 cm. In some further embodiments of the present disclosure, a desired set-point distance may range from 0.1 cm to 10 cm. In still further embodiments of the present disclosure, a desired set-point distance may range from 3 cm to 6 meters.

By way of example, after the set-point value or values are entered, the set-points are stored in the storage means of the user interface. A control system algorithm or protocol then compares the actual value of the variable to the set-point value, and changes an output to minimize the difference between the two. By way of example, the positioning system may measure the actual distance between the front surface of the housing to the target surface, and feed this actual value to the control system. The control system algorithm or protocol then compares the actual distance to the set-point distance and calculates an output value, which is then sent to movement actuating elements in the moveable arm, in this example a robotic arm, to manipulate the positions of the joints so that the actual distance matches the set-point distance within allowable differences. This sequence of events may be repeated at a defined time interval until the actual distance matches the set-point distance.

Similarly, once the desired distance between the front face of the housing and the target surface is attained, the apparatus for delivering electromagnetic radiation may use at least one additional control system algorithm or protocol to adjust the actual power density reaching the target surface to match a set-point power density entered by the user. By way of example, a measuring device comprising an infrared camera may measure a secondary variable, for example surface temperature that may be correlated to the power density impinging upon the target surface. The control system may then take the estimate of, or the actual measured power density, and calculate an output that changes the power density provided by the apparatus to the target. The various types of control algorithms or protocols that may be incorporated into the present disclosure, include but are not limited to, feed-forward control loops and feedback control loops, the details of which are known to one of ordinary skill in the art.

In some embodiments of the present disclosure, the user interface is adapted to interface with, and interact with, a programmable power source, wherein the user or the control system may specify, change and/or manipulate at least one of the amplitude, frequency, duty cycle and/or duration of at least one power signal applied by the power source to at least one of the primary radiation source, the at least one additional radiation source, and the any other radiation sources. The power source may comprise any conventional power source capable of driving the radiation sources of the apparatus (e.g., any power source capable of providing at least one of a driving voltage and a current with a desired amplitude, frequency, duration and/or duty cycle to the radiation sources). In one embodiment, a programmable power source comprising a model No. MS210 four-channel mixer and a model no. PS24 twenty-four volt power supply available from Advanced Illumination of Rochester, Vt., may be used, although any other suitable power source may be similarly employed.

In some embodiments of the present disclosure, the user interface also may be employed to control at least one of the position of a moveable arm, a movement device, a positioning system, and the measuring device. In some embodiments of the present disclosure, the housing, the arm, the movement device, the positioning system, and the measuring device may operate independently, or in cooperation, so as to form an overall target positioning system that may or may not be in communication with a user interface comprising a control system.

Those skilled in the art will understand that devices in communication with each other need only be "capable of" communicating with each other and need not be continually transmitting data to or receiving data from each other. On the contrary, such devices need only transmit data to, or receive data from, each other as necessary, and may actually refrain from exchanging data most the time. Further, devices may be in communication even though steps may be required to establish a communication link. Such communication may be performed over any suitable channel or combination of channels including for example, wireless, hardwired, optical or other channel types.

In some embodiments of the present disclosure, variables such as radiation application times, cycles, etc. may be manipulated and changed. In some embodiments, the electrical current and/or power supplied to at least one of the radiation sources by the power supply may be continuous, so that the radiation sources remain energized during the time that the apparatus is in use, or alternatively, the current/and or power supplied to the at least one of the radiation sources may be supplied as pulses at a rate of from about 1 to 100 pulses/sec. Pulsing the radiation may have the positive benefits of, among other things, minimizing the effects of radiation exposure on surface areas surrounding the target surface, and allowing for a corresponding cycle of warming and cooling periods in the target surface. In still other embodiments of the present disclosure, at least one of the power densities, or energy outputs, of at least one of the radiation sources may be applied in some periodic fashion including, but not limited to, step functions, sinusoidal functions, triangular waves, as well as non-periodic patterns.

Figure 2:
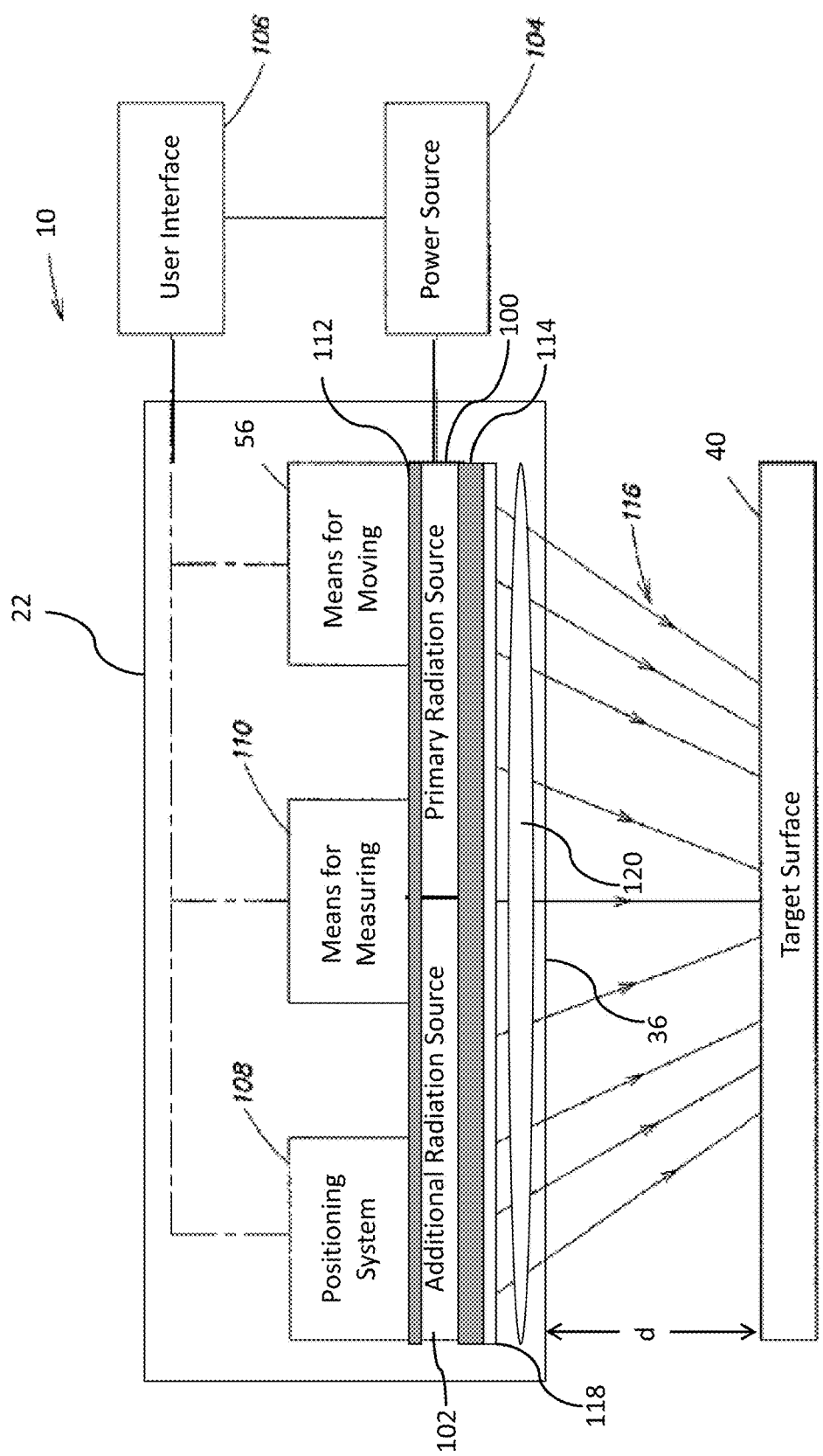
FIG. 2 illustrates the housing of the apparatus of FIG. 1, containing a primary radiation source.

Referring now to FIG. 2, an example of a multifunctional radiation delivery apparatus according to the present disclosure is shown. The housing 22 is positioned at the desired distance d from the target surface 40. In this example, a primary radiation source 100 is positioned adjacent to an additional radiation source 102 in substantially the same plane. A heat sink 112 is positioned above each radiation source. A filter 114 is positioned below both radiation sources, which manipulates electromagnetic radiation 116 in a desired fashion. A power density equalizer 118 is located below the filter 114 to equalize the power emitted by the radiation sources to a desired W/cm². A focusing system 120 is located below the power density equalizer 118, to further manipulate, focus or direct at least a portion of the radiation to a specific portion on the target surface 40. Also located in the housing 22 are a positioning system 108, a measuring device 110, and a movement device 56. It should be clear to one of ordinary skill in the art that some embodiments of the positioning system 108 and the measuring device 110 will require an unobstructed view of the target surface 40, e.g. a laser range finder for the positioning means 108, or an infrared camera for the measuring device 110. Although FIG. 2 does not show such unobstructed views of the target surface 40, it is to be understood that these would be provided in the present disclosure as needed to enable the apparatus to function as intended. The apparatus may also include a power source 104 interconnected with both the primary radiation source 100 and a user interface 106. It should be understood that the relative positions of the components in the housing may be changed as needed, and that these variations fall within the scope of the present disclosure. For example, the power density equalizer 118 may be placed adjacent to the radiation sources 100, 102 with the filter 114 placed below the power density equalizer 118.

In some embodiments of the present disclosure, the multifunction apparatus for delivering electromagnetic radiation is mobile or portable. In some embodiments of the present disclosure, the body may further comprise at least one of a platform, table, wheels, a case, a storage compartment, and combinations thereof.

An aspect of the present disclosure is an apparatus for delivering electromagnetic radiation to a stationary target comprising a housing comprising, a) a front face, b) a primary radiation source, comprising at least one array of light-emitting diodes, wherein each array comprises at least one light-emitting diode, and the primary radiation source provides electromagnetic radiation with a wavelength ranging from about 800 nm to about 950 nm, and a power emitted ranging from about 1.0 W to about 5,000 W, c) at least one additional radiation source, comprising a light-source that is not at least on light-emitting diode, d) a heat sink, wherein the primary radiation source and the at least one additional radiation source are both in physical contact with the heat sink, e) a heat spreader in physical contact with the heat sink, f) a filter positioned adjacent to at least one of the primary radiation source and the at least one additional radiation source, g) a focusing system positioned adjacent to the filter, and h) a power density equalizer positioned adjacent to the focusing system. The apparatus also comprises a moveable arm comprising a first end and a second end with a length spanning between the first end and the second end, a body, wherein the housing is adjustably connected to the first end of the moveable arm, and the body is adjustably connected to the second end of the moveable arm, a movement device, a positioning system comprising a targeting device and a distance-setting device, a measuring device, and a control system for controlling the variable to a set-point, by at least one of adjusting the power emitted and the target distance.

As certain aspects of the disclosure are directed to a method, one of skill in the art will appreciate the multitude of ways the herein referenced devices can be employed. In one particular embodiment, somewhat representative of other methods that employ at least one device described herein, the disclosure includes a method for delivering electromagnetic radiation to a patient comprising the following steps of a) providing a device comprising, i) a housing with a front face, and a primary radiation source and a heat sink positioned with the housing, wherein the primary radiation source provides an emitted power, ii) a moveable arm comprising a first end and a second end with a length spanning between the first end and the second end, iii) a body, wherein the housing is adjustably connected to the first end of the moveable arm, and the body is adjustably connected to the second end of the moveable arm, iv) a movement device, v) a positioning system comprising a targeting device and a distance-setting device, vi) a measuring device, and vii) a control system for controlling the variable to a set-point, by at least one of adjusting the power density and the target distance. Then, in this exemplary embodiment of a method, the electromagnetic radiation is delivered by, a) moving the moveable arm and the housing to enable moving of the front face of the housing relative to the patient, b) targeting the electromagnetic radiation on a target portion of the patient using a positioning system, c) setting the distance between the front face of the housing and the target portion of the patient to a desired target distance, d) measuring a variable of the target portion of the patient, and e) controlling the variable to a set-point by at least one of adjusting the power density and the target distance.

A further aspect of the present disclosure is a method for thermally ablating a target tissue of a patient comprising, a) injecting a mixture comprising gold nanoparticles into the target tissue, wherein the nanoparticles comprise a length ranging from about 30 nm to about 60 nm and a width ranging from about 10 nm to about 14 nm, b) providing a device comprising: i) a housing comprising: a front face, a primary radiation source, comprising at least one array of light-emitting diodes, wherein each array comprises at least one light-emitting diode, and the primary radiation source provides electromagnetic radiation with a wavelength of about 950 nm, and a power emitted ranging from about 1.0 W to about 100 W, and a heat sink, ii) a moveable arm comprising a first end and a second end with a length spanning between the first end and the second end, iii) a body, wherein the housing is adjustably connected to the first end of the moveable arm, and the body is adjustably connected to the second end of the moveable arm, iv) a movement device, v) a positioning system comprising a targeting device and a distance-setting device, vi) a measuring device, and vii) a control system for controlling the variable to a set-point, by at least one of adjusting the power emitted and the target distance.

This exemplary method then further comprises, a) moving the moveable arm and the housing to enable moving of the front face of the housing relative to the target tissue of the patient, b) targeting the electromagnetic radiation on target tissue of the patient using a positioning system, c) setting the distance between the front face of the housing and the target tissue of the patient to a desired target distance, d) radiating the target tissue, e) measuring a variable of the target tissue, and f) controlling the variable to a set-point by at least one of adjusting the power emitted and the target distance, whereby a target tissue temperature is raised by at least 5 degrees Celsius.

The description above is not intended to limit the invention, as one of skill in the art would recognize from the above teachings and their accompanying examples that other techniques and methods can satisfy the claims and can be employed without departing from the scope of the claimed invention.

What is claimed is:

1. A method for thermally ablating a target tissue of a patient consisting of:
   a) injecting a mixture of gold nanoparticles into a target tissue, wherein the nanoparticles have a length of between about 30 nanometers and about 60 nanometers and a width of between about 10 nanometers and about 14 nanometers;
   b) providing a device consisting of:
      i) a housing, having a front face,
      ii) a primary radiation source with an array of light-emitting diodes, wherein the primary radiation source provides electromagnetic radiation with a wavelength of about 950 nanometers, and a power of between about 1 watt and about 100 watts;
      iii) a moveable arm, with a first end and a second end;
      iv) a body;
      v) a movement device;
      vi) a positioning system, with a targeting device and a distance-setting device, wherein the targeting device comprises a reticle;
      vii) a measuring device for collecting measurement data from the target tissue;
      viii) a control system for setting the measurement data from the target portion of the target tissue to a predetermined value by adjusting at least one of a target distance and the power of the electromagnetic radiation provided by the primary radiation source,
      ix) wherein the housing is adjustably interconnected to the first end of the moveable arm and the body is adjustably interconnected to the second end of the moveable arm, and wherein the housing and the body are each one or more of rotatable, slidable, and translatable relative to the moveable arm;
      x) a focusing system adapted to be positioned substantially parallel to and near the surface from which electromagnetic radiation is emitted, said focusing system including an optical component adapted to focus the electromagnetic radiation onto a specific portion of the target tissue, said focusing system controlling a direction in which the electromagnetic radiation emitted by the array of light-emitting diodes propagates so that the electromagnetic radiation travels towards the target tissue, said focusing system having at least one of an internal reflecting lens and a refractive lens;

xi) a heat sink in physical contact with the primary radiation source;

xii) a heat spreader in physical contact with the heat sink; and xiii) a filter positioned adjacent to the primary radiation source;

c) moving the moveable arm and the housing to enable moving of the front face of the housing relative to the target tissue of the patient;

d) targeting the electromagnetic radiation on the target tissue of the patient using the positioning system;

e) setting the distance between the front face of the housing and the target tissue of the patient to the target distance;

f) radiating the target tissue wherein said step of radiating includes the focusing of the electromagnetic radiation emitted by the array of light-emitting diodes onto the target tissue, said step of radiating resulting in the heating of the gold nanoparticles in the target tissue;

g) adjusting a power density reaching the target tissue to match a set-point power density;

h) measuring a variable of the target tissue; and i) setting a variable to a predetermined value by adjusting at least one of the target distance and the power of the electromagnetic radiation provided by the primary radiation source, such that a temperature of the target tissue is raised by at least 5 degrees Celsius.

* * * * *